US005756460A

United States Patent [19]
Evans et al.

[11] Patent Number: 5,756,460
[45] Date of Patent: May 26, 1998

[54] HUMAN GALANIN, CDNA CLONES ENCODING HUMAN GALANIN AND A METHOD OF PRODUCING HUMAN GALANIN

[75] Inventors: Helen Frances Evans, Bondi Junction; John Shine, Woolwich, both of Australia

[73] Assignee: Garvan Institute of Medical Research, Darlinghurst, Australia

[21] Appl. No.: 507,016

[22] Filed: Jul. 25, 1995

Related U.S. Application Data

[63] Continuation of Ser. No. 108,733, Sep. 3, 1993, abandoned.

[30] Foreign Application Priority Data

Mar. 6, 1991 [AU] Australia ................... PK4953

[51] Int. Cl.$^6$ .................. A61K 38/17; C12N 15/12; C12P 21/02
[52] U.S. Cl. .................. 514/12; 536/23.5; 435/69.1; 435/172.3
[58] Field of Search .................. 435/69.1, 172.3, 435/325, 252.3, 254.11, 320.1; 514/12, 2, 866; 536/235; 424/85.1, 570; 530/324, 300

[56] References Cited

FOREIGN PATENT DOCUMENTS

| 8906135 | 7/1989 | WIPO . |
| 9212997 | 8/1992 | WIPO . |
| 9215015 | 9/1992 | WIPO . |

OTHER PUBLICATIONS

Young et al. Proc. Nat. Acad. Sci., USA 80: 1194–1198, 1983.
Loche et al. Pediatric Res. 26:316–319, 1989.
Bauer et al. Gastroenterology 91: 877–883, 1986.
Hermansen et al. Acta Endrocrinologica 121:541–550, 1989.
Davis et al. J. Clin. Endocrin. Metab. 65: 1248–1252, 1987.
Fisone et al. Proc. Nat. Acad. Sci. USA 86: 9588–9589, 1988.
Gallwitz et al. Biochem. Biophys. Res. Comm. 172: 268–275, 1990.
Lagny–Pourmir et al. Peptides 10:757–761, 1989.
Vrontakis et al., J. Biol. Chem., 262:35, 1987, pp. 16755–16758.
Rökaeus, et al., Proc. Natl. Acad. Sci. USA, vol. 83, pp. 6287–6291, 1986.
Bersani, et al., FEBS Letters, vol. 283, No. 2, pp. 189–194, 1991.
Rökaeus, et al., FEBS Letters, vol. 234, No. 2, pp. 400–406, 1988.
Schmidt et al., Proc. Natl. Acad. Sci. USA, vol. 88, pp. 11435–11439, 1991.
Ulman, et al., Neuroscience Letters, 136, pp. 105–108, 1992.
Kaplan, et al., Proc. Natl. Acad. Sci. USA, 85, pp. 1065–1069, 1988.

*Primary Examiner*—Robert A. Wax
*Assistant Examiner*—G. E. Bugaisky
*Attorney, Agent, or Firm*—Rothwell, Figg, Ernst & Kurz

[57] ABSTRACT

The present invention provides a peptide having the amino acid sequence of human galanin. The amino acid sequence of this peptide is: GWTLNSAGYLLGPHAVGNHRSFSD-KNGLTS (SEQ ID NO: 1). The present invention further provides DNA clones encoding the peptide and to therapeutic uses of the peptide.

5 Claims, 6 Drawing Sheets

```
Base Pair Number                                              -20        -10
               *         *         *         *         *
  5                                                       AGCGCAGCTCAAG
         10        20        30        40        50        60
          *         *         *         *         *         *
ATGGCCCGAGGCAGCGCCCTCCTGCTCGCCTCCCTCCTCCTCGCCGCGGCCCTTTCTGCC
MetAlaArgGlySerAlaLeuLeuLeuAlaSerLeuLeuLeuAlaAlaAlaLeuSerAla 70        80        90       100       110       120
          *         *         *         *         *         *
TCTGCGGGGCTCTGGTCGCCGGCCAAGGAAAAACGAGGCTGGACCCTGAACAGCGCGGGC
SerAlaGlyLeuTrpSerProAlaLysGluLysArgGlyTrpThrLeuAsnSerAlaGly 130       140       150       160       170       180
          *         *         *         *         *         *
TACCTGCTGGGCCCACATGCCGTTGGCAACCACAGGTCATTCAGCGACAAGAATGGCCTC
TyrLeuLeuGlyProHisAlaValGlyAsnHisArgSerPheSerAspLysAsnGlyLeu
                    HUMAN GALANIN 190       200       210       220       230       240
          *         *         *         *         *         *
ACCAGCAAGCGGGAGCTGCGGCCCGAAGATGACATGAAACCAGGAAGCTTTGACAGGTCC
ThrSerLysArgGluLeuArgProGluAspAspMetLysProGlySerPheAspArgSer
              GALANIN mRNA ASSOCIATED PEPTIDE 250       260       270       280       290       300
          *         *         *         *         *         *
ATACCTGAAAACAATATCATGCGCACAATCATTGAGTTTCTGTCTTTCTTGCATCTCAAA
IleProGluAsnAsnIleMetArgThrIleIleGluPheLeuSerPheLeuHisLeuLys 310       320       330       340       350       360
          *         *         *         *         *         *
GAGGCCGGTGCCCTCGACCGCCTCCTGGATCTCCCCGCCGCAGCCTCCTCAGAAGACATC
GluAlaGlyAlaLeuAspArgLeuLeuAspLeuProAlaAlaAlaSerSerGluAspIle 370       380       390       400       410       420
          *         *         *         *         *         *
GAGCGGTCCTGAGAGCCTCCTGGGCATGTTTGTCTGTGTGCTGTAACCTGAAGTCAAACC
GluArgSerEnd 430       440       450       460       470       480
          *         *         *         *         *         *
TTAAGATAATGGATAATCTTCGGCCAATTTATGCAGAGTCAGCCATTCCTGTTCTCTTTG 490       500       510       520       530       540
          *         *         *         *         *         *
CCTTGATGTTGTGTTGTTATCATTTAAGATTTTTTTTTTTTTTTGGTAATTATTTTGAGTG 550       560
          *         *
GCAAAATAAAGAATAGCAATTA(n)
```

FIG.1

|  | 1 | 2 | 3 | 4 | 5 | 6 | 7 | 8 | 9 | 10 | 11 | 12 | 13 |
|---|---|---|---|---|---|---|---|---|---|---|---|---|---|
| human GA1 | GLY- | TRP- | THR- | LEU- | ASN- | SER- | ALA- | GLY- | TYR- | LEU- | LEU- | GLY- | PRO |
| bovine |
| poraine |
| rat |

|  | 14 | 15 | 16 | 17 | 18 | 19 | 20 | 21 | 22 | 23 | 24 | 25 | 26 |
|---|---|---|---|---|---|---|---|---|---|---|---|---|---|
| human | HIS- | ALA- | VAL- | GLY- | ASN- | HIS- | ARG- | SER- | PHE- | SER- | ASP- | LYS- | ASN- |
| bovine | | | | | LEU- | ASP- | SER- | | | GLN- | | | HIS- |
| poraine | | | | | ILE- | ASP- | ASN- | | | HIS- | | | TYR- |
| rat | | | | | ILE- | ASP- | ASN- | | | SER- | | | HIS- |

|  | 27 | 28 | 29 | 30 |
|---|---|---|---|---|
| human GA1 | GLY- | LEU- | THR- | SER |
| bovine | | | ALA- | NH2 |
| poraine | | | ALA- | NH2 |
| rat | | | THR- | NH2 |

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 30 amino acids
        (B) TYPE: amino acid
        (D) TOPOLOGY: linear     (ii) MOLECULE TYPE: peptide     (iii) HYPOTHETICAL: NO     (v) FRAGMENT TYPE: N-terminal     (xi) SEQUENCE DESCRIPTION: SEQ ID NO:1:

```
Gly Trp Thr Leu Asn Ser Ala Gly Tyr Leu Leu Gly Pro His Ala Val
 1               5                  10                  15
Gly Asn His Arg Ser Phe Ser Asp Lys Asn Gly Leu Thr Ser
                20                  25                  30
```

(2) INFORMATION FOR SEQ ID NO:2:

(i) SEQUENCE CHARACTERISTICS:
        (A) LENGTH: 29 amino acids
        (B) TYPE: amino acid
        (D) TOPOLOGY: linear     (ii) MOLECULE TYPE: peptide     (iii) HYPOTHETICAL: NO     (v) FRAGMENT TYPE: N-terminal     (xi) SEQUENCE DESCRIPTION: SEQ ID NO:2:

```
Gly Trp Thr Leu Asn Ser Ala Gly Tyr Leu Leu Gly Pro His Ala Leu
 1               5                  10                  15
```

```
        Asp  Ser  His  Arg  Ser  Phe  Gln  Asp  Lys  His  Gly  Leu  Ala
                       20                       25
```

(2) INFORMATION FOR SEQ ID NO:3:

(i) SEQUENCE CHARACTERISTICS:
        (A) LENGTH: 29 amino acids
        (B) TYPE: amino acid
        (C) STRANDEDNESS: single
        (D) TOPOLOGY: linear     (ii) MOLECULE TYPE: protein     (iii) HYPOTHETICAL: NO     (v) FRAGMENT TYPE: N-terminal     (xi) SEQUENCE DESCRIPTION: SEQ ID NO:3:

```
  Gly  Trp  Thr  Leu  Asn  Ser  Ala  Gly  Tyr  Leu  Leu  Gly  Pro  His  Ala  Ile
   1                  5                       10                            15
  Asp  Asn  His  Arg  Ser  Phe  His  Asp  Lys  Tyr  Gly  Leu  Ala
                       20                       25
```

(2) INFORMATION FOR SEQ ID NO:4:

(i) SEQUENCE CHARACTERISTICS:
        (A) LENGTH: 29 amino acids
        (B) TYPE: amino acid
        (C) STRANDEDNESS: single
        (D) TOPOLOGY: linear     (ii) MOLECULE TYPE: peptide     (iii) HYPOTHETICAL: NO     (v) FRAGMENT TYPE: N-terminal     (xi) SEQUENCE DESCRIPTION: SEQ ID NO:4:

```
  Gly  Trp  Thr  Leu  Asn  Ser  Ala  Gly  Tyr  Leu  Leu  Gly  Pro  His  Ala  Ile
   1                  5                       10                            15
  Asp  Asn  His  Arg  Ser  Phe  Ser  Asp  Lys  His  Gly  Leu  Thr
                       20                       25
```

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: both
        (D) TOPOLOGY: linear     (ii) MOLECULE TYPE: DNA     (iii) HYPOTHETICAL: NO     (iv) ANTI-SENSE: NO     (xi) SEQUENCE DESCRIPTION: SEQ ID NO:5:

```
GAATTCAAGG ARAAGAGAGG CTGGACYCTG AA                                           32
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: both
        (D) TOPOLOGY: linear     (ii) MOLECULE TYPE: DNA (genomic)

(i i i) HYPOTHETICAL: NO (i v) ANTI-SENSE: NO (x i) SEQUENCE DESCRIPTION: SEQ ID NO:6:

CCATAAGCTT GCSCCSGCNT CTTTRAGRTG CARGAA    36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: both
        (D) TOPOLOGY: linear     (i i) MOLECULE TYPE: DNA (genomic)

(i i i) HYPOTHETICAL: NO

(i v) ANTI-SENSE: NO

(x i) SEQUENCE DESCRIPTION: SEQ ID NO:7:

CCATAAGCTT AATGAYCTGT GGYTGTCRAK SGCATG    36

(2) INFORMATION FOR SEQ ID NO:8:

(i) SEQUENCE CHARACTERISTICS:
        (A) LENGTH: 575 base pairs
        (B) TYPE: nucleic acid
        (C) STRANDEDNESS: both
        (D) TOPOLOGY: linear     (i i) MOLECULE TYPE: DNA     (i i i) HYPOTHETICAL: NO     (i x) FEATURE:
        (A) NAME/KEY: CDS
        (B) LOCATION: 14..385

(x i) SEQUENCE DESCRIPTION: SEQ ID NO:8:

```
AGCGCAGCTC AAG ATG GCC CGA GGC AGC GCC CTC CTG CTC GCC TCC CTC       49
            Met Ala Arg Gly Ser Ala Leu Leu Leu Ala Ser Leu
             1               5                  10

CTC CTC GCC GCG GCC CTT TCT GCC TCT GCG GGG CTC TGG TCG CCG GCC       97
Leu Leu Ala Ala Ala Leu Ser Ala Ser Ala Gly Leu Trp Ser Pro Ala
         15                  20                  25

AAG GAA AAA CGA GGC TGG ACC CTG AAC AGC GCG GGC TAC CTG CTG GGC      145
Lys Glu Lys Arg Gly Trp Thr Leu Asn Ser Ala Gly Tyr Leu Leu Gly
     30                  35                  40

CCA CAT GCC GTT GGC AAC CAC AGG TCA TTC AGC GAC AAG AAT GGC CTC      193
Pro His Ala Val Gly Asn His Arg Ser Phe Ser Asp Lys Asn Gly Leu
 45                  50                  55                  60

ACC AGC AAG CGG GAG CTG CGG CCC GAA GAT GAC ATG AAA CCA GGA AGC      241
Thr Ser Lys Arg Glu Leu Arg Pro Glu Asp Asp Met Lys Pro Gly Ser
             65                  70                  75

TTT GAC AGG TCC ATA CCT GAA AAC AAT ATC ATG CGC ACA ATC ATT GAG      289
Phe Asp Arg Ser Ile Pro Glu Asn Asn Ile Met Arg Thr Ile Ile Glu
         80                  85                  90

TTT CTG TCT TTC TTG CAT CTC AAA GAG GCC GGT GCC CTC GAC CGC CTC      337
Phe Leu Ser Phe Leu His Leu Lys Glu Ala Gly Ala Leu Asp Arg Leu
     95                  100                 105

CTG GAT CTC CCC GCC GCA GCC TCC TCA GAA GAC ATC GAG CGG TCC TGAGA   387
Leu Asp Leu Pro Ala Ala Ala Ser Ser Glu Asp Ile Glu Arg Ser
 110                 115                 120

GCCTCCTGGG CATGTTTGTC TGTGTGCTGT AACCTGAAGT CAAACCTTAA GATAATGGAT   447
```

-continued

```
AATCTTCGGC CAATTTATGC AGAGTCAGCC ATTCCTGTTC TCTTTGCCTT GATGTTGTGT    507

TGTTATCATT TAAGATTTTT TTTTTTTTG GTAATTATTT TGAGTGGCAA AATAAAGAAT     567

AGCAATTA                                                             575
```

( 2 ) INFORMATION FOR SEQ ID NO:9:

( i ) SEQUENCE CHARACTERISTICS:
        ( A ) LENGTH: 123 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:9:

```
Met Ala Arg Gly Ser Ala Leu Leu Leu Ala Ser Leu Leu Leu Ala Ala
 1               5                  10                  15

Ala Leu Ser Ala Ser Ala Gly Leu Trp Ser Pro Ala Lys Glu Lys Arg
                20                  25                  30

Gly Trp Thr Leu Asn Ser Ala Gly Tyr Leu Leu Gly Pro His Ala Val
            35                  40                  45

Gly Asn His Arg Ser Phe Ser Asp Lys Asn Gly Leu Thr Ser Lys Arg
        50                  55                  60

Glu Leu Arg Pro Glu Asp Met Lys Pro Gly Ser Phe Asp Arg Ser
 65                 70                  75                  80

Ile Pro Glu Asn Asn Ile Met Arg Thr Ile Ile Glu Phe Leu Ser Phe
                85                  90                  95

Leu His Leu Lys Glu Ala Gly Ala Leu Asp Arg Leu Leu Asp Leu Pro
            100                 105                 110

Ala Ala Ala Ser Ser Glu Asp Ile Glu Arg Ser
            115                 120
```

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( D ) TOPOLOGY: linear     ( i i ) MOLECULE TYPE: peptide     ( i i i ) HYPOTHETICAL: NO     ( v ) FRAGMENT TYPE: N-terminal     ( x i ) SEQUENCE DESCRIPTION: SEQ ID NO:10:

```
Gly Trp Thr Leu Asn Ser Ala Gly Tyr Leu Leu Gly Pro His Ala Val
 1               5                  10                  15

Asn His Arg Ser Phe Ser Asp Lys Asn Gly Leu Thr Ser
                20                  25
```

HUMAN GALANIN, CDNA CLONES ENCODING HUMAN GALANIN AND A METHOD OF PRODUCING HUMAN GALANIN

This is a continuation of application Serial No. 08/108,733, filed Sep. 3, 1993 now abandoned, which is a U.S. 371 of PCT/AU 92/0097.

FIELD OF THE INVENTION

The present invention relates to a peptide having the amino acid sequence of human galanin as deduced from the nucleotide sequence of human preprogalanin CDNA. The present invention further relates to CDNA clones encoding the peptide. In addition, the present invention encompasses therapeutic uses of the peptide, and the use of the peptide in designing galanin antagonists and agonists.

BACKGROUND OF THE INVENTION

Galanin is a putative neuropeptide which was first isolated from porcine small intestine in 1983(1). Porcine galanin is a peptide of 29 amino acid residues which was named for its N-terminal glycine and amidated C-terminal alanine residues (1). The cDNAs encoding galanin have been cloned from three species, rat (2), porcine (3) and bovine (4), revealing that galanin is a proteolytic product of a larger precursor protein known as preprogalanin (2). Galanin shows 90% homology between the species but little similarity to other known peptides (1). Antibodies raised to porcine galanin have allowed the mapping of galanin-like-immunoreactivity (GAL-LI) to discrete regions of the Central Nervous System (CNS) and throughout the Peripheral Nervous System (PNS) of several other species including man.

Immunohistochemical mapping of GAL-LI in the CNS has been performed most intensively in the rat where the highest concentrations have been found in the median eminance and hypothalamus (5). These results are consistent with more recent in situ hybridisation studies where the localisation of preprogalanin in the rat brain tentatively suggests the involvement of galanin in the feeding regulation of several factors ranging from water balance behaviour to blood pressure control (6). Similarly, radioimmunoassay of galanin in the baboon brain showed high GAL-LI in the hypothalamus and median eminance, and also GAL-LI in association with limbic structures such as the amygdala (7). Immunohistochemistry and in situ studies of preprogalanin mRNA during development of the rat has shown tissue specific sex differences in galanin concentration, notably in the anterior pituitary (5) where its expression is eostrogen dependent (9). The overall distribution of GAL-LI and its colocalisation in discrete neuronal cells with catecholamines, serotonin, GABA, acetylcholine and various other peptides (10) strongly suggest a modulatory role for galanin. A noteworthy example is the coexistence of galanin with acetylcholine in nerve fibers projecting from the basal forebrain to the hippocampus, in the rat (11) and baboon (7) which has led to speculation that galanin may play a role in Alzheimers disease. There is, however, conflicting evidence concerning the expression of galanin in this region of the human brain. Although the physiological role of galanin in the CNS has not yet been established its pharmacology suggests a role in neuroendocine regulation. Injection of galanin into the third ventricle of rats causes increased growth hormone (13) and injection into the paraventricular nucleus (PVP) enhances food intake (14).

In the PNS, distribution of GAL-LI suggests that galanin is widespread. Galanin distribution and its pharmacology, which is diverse and often species specific, both suggest a range of physiological actions for galanin. However, some confusion may have arisen as to its pharmacological role through the use of porcine galanin in experiments involving other species. In numerous mammalian species the highest concentrations of GAL-LI are found in the intestine (1), pancreas (15), adrenal glands (3), and respiratory (16) and genitourinary tracts (17). Galanin action on the pancreas and its possible role in diabetes is controversial; it has been established that porcine galanin infusion in dogs (15), and rat and porcine galanin perfusion through the isolated rat pancreas (18), decrease plasma insulin levels. However there are conflicting results concerning porcine galanin action on the pig pancreas (19). In the dog galanin also decreases somatostatin while increasing glucagon but this may not be the case in other species (15). Intravenous porcine galanin causes growth hormone secretion in a variety of species including man. However, intravenous porcine galanin infusion in man at a concentration sufficiently high to elicit an increase in growth hormone levels, does not cause the expected inhibition of insulin (20). The apparent discrepancy may be due to the difference in amino acid sequence of human verses porcine galanin, or it may be simply a reflection of the species specific effects of galanin. Visualisation of GAL-LI in neurons innervating the islets of several species (15) added to a proposal to explain the galanin induced inhibition of insulin secretion in rat B-cell lines (21) support a neuromodulatory role for galanin on endocrine pancreatic action. Other pharmacological effects of galanin in the PNS include the species specific stimulatory or inhibitory action of galanin on the smooth muscle activity of several mammalian species (22).

Galanin receptors have been identified in a hamster insulin-secreting B-cell tumor (23), rat (24) and monkey brain (25), and smooth muscle membranes (22). The distribution of galanin binding correlates with that of GAL-LI and therefore supports the role of galanin in neurotransmission. It is not clear whether there are subtypes of the galanin receptor, nor which region of the peptide is responsible for binding to its receptor. Studies on the biological effect of tryptic fragments of galanin on smooth muscle preparations (22), in addition to auto-radiographic binding studies on Rin 5 mf pancreatic B cell-lines (26) and on intestinal membrane preparations (27), present conflicting results.

The molecular biology of the galanin gene has not yet been examined in humans. Porcine preprogalanin is a 123 amino acid residue protein that comprises a signal sequence, galanin (29 amino acids) and a 59 amino acid peptide known as galanin mRNA associated peptide (GMAP). The length and structure of rat porcine and bovine preprogalanin are similar. The 20% difference in galanin amino acid homology across the species is manifest over the C-terminal end of the peptide. The sequence in all species identified to date suggests post translational cleavage of glycine extended galanin followed by amidation. GMAP is also well conserved across the species which has led to speculation that it is biologically active; it includes a region of 35 amino acids that shows 78% homology across the species and within this region stretch of 17 residues that shows greater homology.

This invention discloses the isolation and characterisation of human preprogalanin from a neuroblastoma cell line cDNA library and from a pituitary cDNA library (28). Oligonucleotides complementary to two conserved regions of pig and rat preprogalanin were used in a polymerase chain reaction (PCR) to specifically amplify the corresponding sequence from neuroblastoma and pituitary cDNA. The two amplification oligonucleotides used (No. 1 and 2) correspond to amino acids 29–37 and 105–97 of rat and pig preprogalanin respectively, and flank a 230 basepair region encoding galanin and the N-terminus of GMAP (FIG. 1) (29). An additional oligonucleotide (No. 3) within this region was used to probe for the correct PCR product (30). The amplified region from both sources of DNA was subcloned and then sequenced (31), revealing identical sequences. The region amplified from neuroblastoma cDNA was used as a probe to isolate clones encoding the complete preprogalanin cDNA from this library (32). Later, the pituitary cDNA library was screened with the same probe, in order to ascertain that any amino acid differences apparent between human preprogalanin and other species, were not due to the erroneous translation of DNA in the neuroblastoma cultured cell line.

The primary structure of human preprogalanin cDNA clones isolated from both libraries were identical but different to that of pig, cow and rat. In general, amino acid substitutions only occurred at positions; noted for variability amongst the other species (FIG. 2), thus confirming that galanin, and GMAP to a lesser extent, are both well conserved. However, several of these changes (e.g. 17, 23 and 26 in galanin) involve amino acids with very different physical and chemical properties suggesting that such changes are important for the correct function of human galanin. Also important is that human galanin is rendered unicue by the striking substitution of a serine for a glycine residue at the C-terminus of galanin, directly proceeding the lys-arg cleavage site in the precursor protein. This implies that human galanin is not amidated at its C-terminus, in contrast to other species, where the glycine residue serves as an amide donor to the proceeding residue after proteolysis. Consequently, human galanin may have a variety of biological properties that differ from porcine, rat, and bovine galanin.

SUMMARY OF THE INVENTION

Accordingly, in a first aspect the present invention consists in a polypeptide having the following amino acid sequence:

GWTLNSAGYLLGPHAVGNHRSFSDKNGLTS (SEQ ID NO: 1)

or a functional equivalent thereof or a fragment thereof.

In a preferred embodiment of the present invention the polypeptide fragment has the amino acid sequence:

GWTLNSAGYLLGPHAVNHRSFSDKNGLTS (SEQ ID NO: 10)

As used herein in relation to polypeptide sequences the term "functional equivalent" is intended to cover minor variations in the amino acid sequence which do not deleteriously affect the biological activity of the polypeptide. It will be recognised by those skilled in the art that a number of modifications may be made to the peptide of the present invention without deleteriously affecting the biological activity of the peptide. This may be achieved by various changes, such as insertions, deletions and substitutions, either conservative or non-conservative in the peptide sequence where such changes do not substantially decrease the biological activity of the peptide. By conservative substitutions the intended combinations are:

G,A; V,I,L,M; D,E; N,Q; S,T; K,R,H;

and

F,Y,W.

It may also be possible to add various groups to the peptide of the present invention to confer advantages such as increased potency or extended half-life in vivo without substantially decreasing the biological activity of the peptide. Peptides designed to perform these functions are described as galanin agonists. These additions and changes include the introduction of D-amino acid residues and the formation of cyclic analogues.

Figure 1:
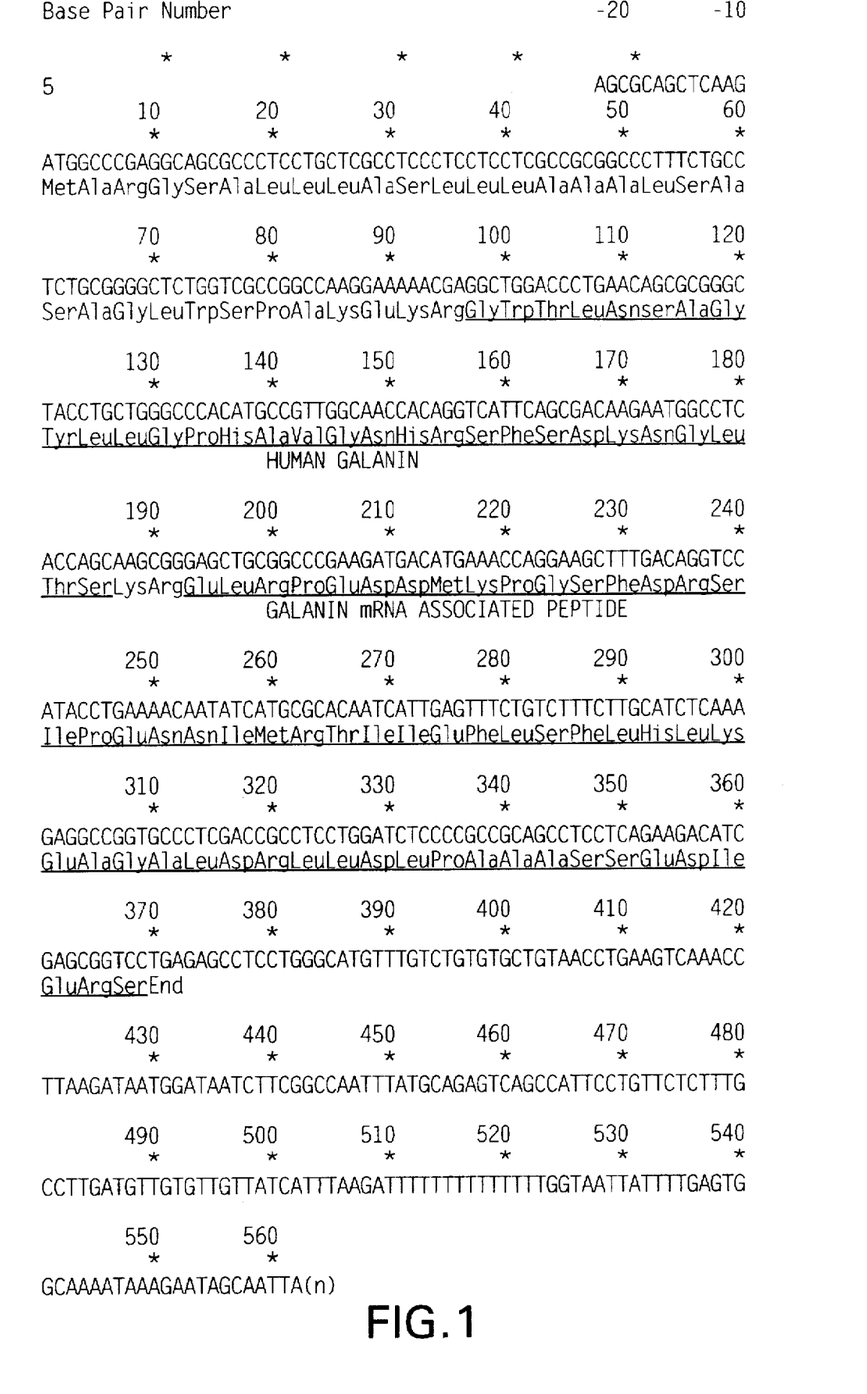
FIG. 1 shows the nucleotide sequence of preprogalanin, the amino acid sequence of human galanin and GMAP (SEQ ID NO: 8.

In a second aspect the present invention consists in a cDNA molecule encoding the peptide of the present invention, the cDNA molecule having a sequence substantially as shown in FIG. 1 from nucleotide 97 to 186 or a functionally equivalent sequence.

In a third aspect the present invention consists in a DNA molecule encoding human preprogalanin and GMAP, the DNA molecule having a sequence substantially as shown in FIG. 1 or a functionally equivalent sequence.

As used herein in relation to DNA sequences the term "functionally equivalent sequence" is intended to cover minor variations in the DNA sequence which, due to degeneracy in the DNA code, do not result in the sequence encoding different polypeptide.

Further, this term is intended to cover alterations in the DNA code which lead to changes in the encoded peptide, but in which such changes do not effect the biological activity of the peptide.

A different half life for human galanin in vivo can be expected, in addition to differences in binding affinity for specific receptors and thus potency between different species.

Of particular interest will be the effect of human galanin on insulin inhibition. Infusion of both porcine and rat galanin through an isolated rat pancreas showed that both types of galanin inhibited insulin and somatostatin release, although porcine galanin was less potent than rat galanin (18). In addition, rat galanin enhanced glucagon secretion whereas porcine galanin was ineffectual. The difference in activity of pig and rat galanin has been ascribed to the 4 amino acid differences that exist between them at their C-terminus. Similarly, the 5 amino acids that differ between human and porcine galanin, coupled with the difference due to amidation, may be responsible for the lack of expected insulin inhibition observed when porcine galanin was infused into human subjects (20). Controversy concerning galanin action on the pancreas, and other examples of the species specific effect of galanin, such as the effect of galanin on the GI tract, indicate that it is preferable to use galanin homologous to the species under investigation.

In a fourth aspect the present invention consists in a method of producing human galanin comprising culturing a cell transformed with the cDNA molecule of the second or third aspect of the present invention under conditions which allow expression of the DNA sequence and recovering the human galanin.

While it is possible to form the polypeptide of the present invention by biological means involving recombinant techniques in prokaryotic or eucaryotic cells the polypeptides may also be formed by chemical synthesis. The decision as to which route of synthesis is used will depend primarily on the length of peptide to be synthesised.

From preliminary results it is clear that the polypeptide of the present invention has therapeutic application in modulating pancreatic activity, as a stimulator of growth hormone and as an attenuator of cardiac vagal function.

Accordingly, in further aspects the present invention consists in a method of modulating pancreatic activity, stimulating the production of growth hormone or attenuating cardiac vagal function in a human comprising administering the peptide of the present invention to the human.

The present invention also consists in the use of the polypeptide of the present invention in the preparation of a medicament for modulating pancreatic activity, stimulating the production of growth hormone or the attenuation of cardiac vagal function.

It has been demonstrated that galanin antagonists can be developed by chemical synthesis of chimeric galanin-like peptides. The N-terminal galanin fragment (amino acids 1–13), which binds the galanin receptor, can be coupled to a peptide of an a-helical structure that stabilises the N-terminal portion but has no innate biological action. The resulting chmiera is described as a galanin antagonist, since it will bind but not activate the galanin receptor, thus inhibiting the action of endogenous galanin. The ability of such a chimeric peptide to function as galanin antagonist can be assessed by measuring its binding efficiency to galanin receptors expressed in RIN mSP cells and the ability to reverse the inhibited insulin response to galanin. A galanin antagonist will displace 125I-galanin binding from RIN m5F cells in a dose dependent manner and reverse the inhibited glucose-induced insulin response to galanin. The antagonist functions as a competitor to galanin but has no effect itself on glucose-induced insulin secretion.

Using the polypeptide of the present invention it will be possible to screen peptides other compounds for galanin agonist and antagonist activity. This would be doen by receptors impressed in RIN m5F cells. The compounds which showed competitive binding would then be assesses for biological activity.

In another aspect the present invention consists in a method of screening compounds for galanin agonist or antagonist activity comprising assessing the ability of the compound to compete with the peptide of the present invention for binding to cell receptors and assessing the biological of the compounds which competitively bind.

The present invention also relates to galanin antagonists obtained by this screening method.

BRIEF DESCRIPTION OF THE DRAWINGS

In order that the present invention may be more clearly understood, preferred forms thereof will now be described with reference to the following examples and accompanying Figures in which.

EXAMPLES

MATERIALS AND METHODS cDNA Libraries

Two cDNA libraries were used for library screening and also as a source of template DNA for a polymerase chain reaction (PCR). The neuroblastoma cDNA library (cat No. HL1007, Clontech Laboratories Inc., USA) contained 1.05× 10⁶ independent clones inserted into a λgt 10 vector at its EcoRI cloning site. The pituitary cDNA library was obtained from Dr P. Seeburg (centre for Molecular Biology, University of Heidelberg, FRG) and was also carried in λgt 10 and cloned in the EcoRI site.

Oligonucleotide Synthesis

With the exception of oligonucleotides directed to the EcoRI cloning site of λgt 10 (Promega, VIC., Australia), all oligonucleotides were prepared on a DNA synthesiser (Applied Bio-systems, DNA synthesiser Model 380B, Burwood, Australia). oligonucleotide sequence:

1. GAATTCAAGGA(A/G)AAGAGAGGCTGGAC(T/C)CTGAA. (EcoRI site incorporated) (SEQ ID NO: 5)
2. CCATAAGCTTGC(G/C)CC(G/C)GC(G/A/T/C)TCTTT(A/G)AG(A/G)TGCA(G/A)GAA (HindIII site incorporated) (SEQ ID NO: 6).
3. CCATAAGCTTAATGA(C/T)CTGTGG(C/T)TGTC (A/G)A(T/G) (C/G)GCATG (HindIII site incorporated) (SEQ ID NO: 7)

Polymerase chain reaction (PCR)

In order to prepare template CDNA, a plate lysate method was used to propagate phage (T. Maniatis, E. F. Fritsch, J. Sambrook, Molecular Cloning: A Lab Manual, 2Ed., Cold Spring Harbour Press, USA, 2.65 (1989)). The libraries were plated at 20,000 plaques per 150 mm diameter plate and extracted into storage medium (SM=0.1M NaCl/0.008M NgSO₄7H₂O/0.05M Tris.HCl/0.02% gelatin) which gave a preparation with a titre of 1×10⁹ phage per ml. The phage stock (2 ml) was extracted with phenol/CHCl₃ and then precipitated with ethanol.

The PCR was used to amplify a 230 base pair region of preprogalanin from the neuroblastoma CDNA library (oligos 1 and 2) and also to amplify the cDNA library clones (λgt10 oligos) that were later isolated by screening. In both reactions, a Hybaid intelligent heating block (Model 1EB 2024, Hybaid, Middx., UK) was used with the following temperature parameters: hold at 95 C. (5'), then 25 cycles of 9° C. (1'), 42° C. (1') and 72° C. (1'). Each reaction contained KCl (50 mM), gelatin (100 µg/ml), MgCl₂ (1.5 mM), Tris-HCl (pH=8, 10 mM), DNA (10 ng–100 µg), dNTP (200µM), Tth polymerase (0.25 U, Toyobo, Japan) and oligonucleotides (500 uM).

PCR products were separated on a 3% Nuseive gel (FMC Bioproducts, ME, USA) (products less than 500 basepairs) or 1% agarose (products greater 700 basepairs). The identity of PCR product bands was established by Southern blotting (E Southern, J. Mol. Biol, 98, 503 (1975)) the DNA onto a nylon membrane (Zeta probe, Bio-Rad Laboratories Inc., CA, USA) using 0.4M NaOH as the transfer buffer followed by hybridisation with oligo #3. Pre-hybridisation was performed at 42°C. in a solution of 5×SSPE (1×SSPE=0.18M NaCl, 10 mM NaH₂PO₄/1 mM NaEDTA pH=7), 0.5% sodium dodecyl sulphate (SDS) and 5×Denhardt's solution (1×Denhardt's solution=0.02% Ficoll-400/0.02% bovine serum albumin/0.02% polyvinylpyrolidone-40) and 100 µg/ml heat denatured salmon sperm DNA. Hybridisation was performed in the same solution with the addition of probe for 6–12 hours at 42° C. The oligo was labelled with γ³² ATP Amersham, International Plc, UK) using T4 polynucleotide kinase (BRL, MD, USA). Blots were washed at 37° C. in 1×(1×SSC=0.151M NaCl/0.1675M tri-sodium citrate)/0.1% SDS prior to exposure to X-ray film (Kodak Eastman, NY, USA) at −70°C. with an intensifying screen for 12 hours. Subclonina and sequencing:

PCR products were separated on a gel as described above. The appropriate band was excised and purified by using gene clean (Bio 101, CA, USA), before restriction digestion. The PCR product generated by preprogalanin oligos 1 and 2 was digested with HindIII and EcoRI, whereas the PCR product generated with the γt10 oligos was digested with EcoRI, before ligation into M13mp19. The M13mp19 subclones were used to transform JM101 competent cells (Maniatis, 1.82–1.84) and subsequently single stranded DNA was prepared using standard methods (Maniatis, 4.29–4.30) for sequencing (kit No. Q5800, Promega). Sequencing difficulties due to secondary structure were overcome with the use of Taq DNA polymerase (kit No. Q 5540, Promega), as the sequencing enzyme at a reaction temperature of 70° C.

cDNA Library Screening

The CDNA libraries described above were screened with the 230 base pair PCR product encoding the sequence of neuroblastoma preprogalanin. The probe was excised from a gel and purified using gene clean before labelling (25 ng) with α32 dCTP in a random priming reaction (kit No. 8187SA, BRL) Approximately 6×10⁵ plaques were plates on 2YT plates (A3, Maniatis) lifted onto High Bond N nylon filters (Amersham) and fixed according to the manufacturer's recommendations. Pre-hydridisation and hybridisation were performed at 65° C. as described above. Filters were washed to a stringency of 0.1% SDS/0.1% SSC at 65° C. and exposed overnight to X-ray film with itensifying screens.

Blood Glucose and Secretion of Gluco-Regulatory Hormones The Administration of Human Galanin to Conscious Rats Rats were maintained on established diets and cannulated under anaesthesia. The rats were then allowed to recover and infused with glucose. Ten minutes later a bolus dose of human galanin was administered and blood samples were taken over the next three hours. Following the sampling procedures the animals were sacrificed.

Figure 2:
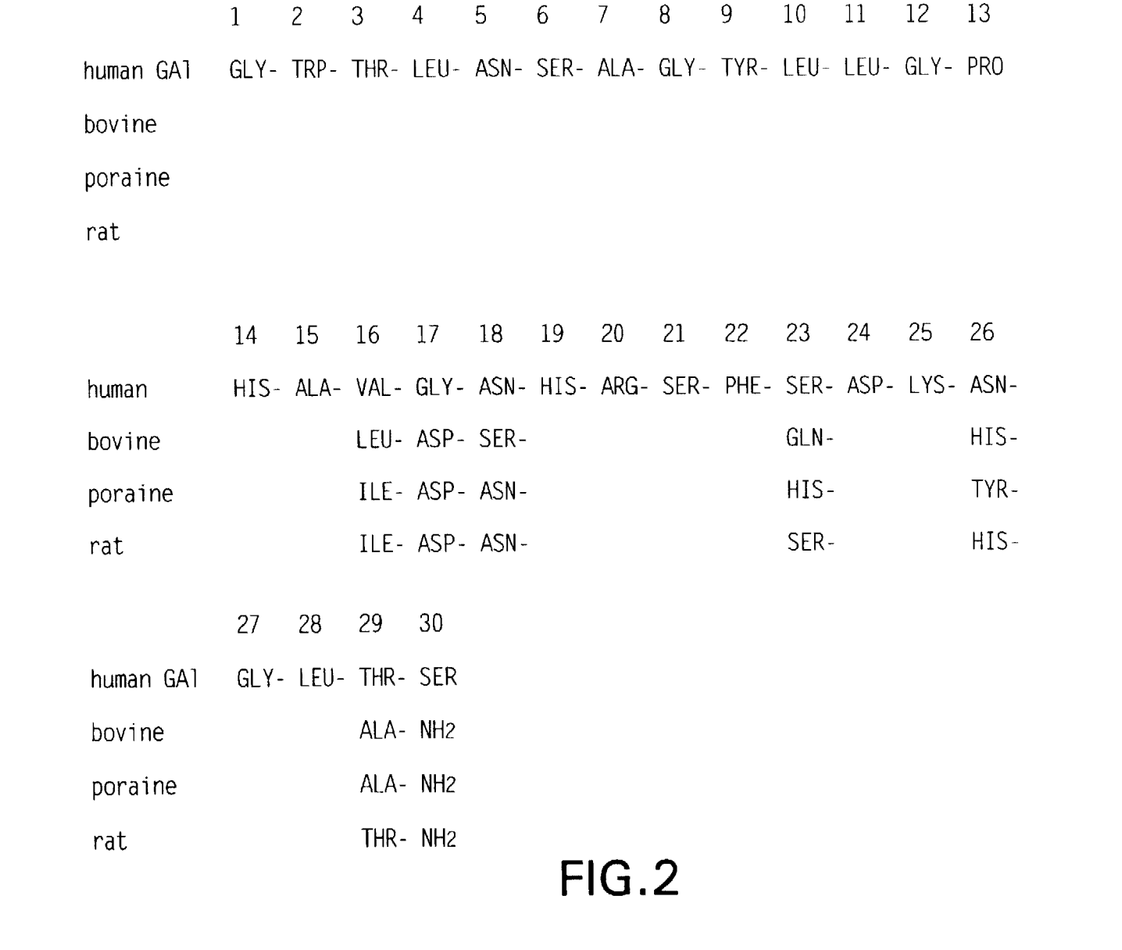
FIG. 2 provides a comparison of the amino acid sequence of human galanin ( SEQ ID NO: 1) with that of bovine (SEQ ID NO: 2), porcine. (SEQ ID NO: 4) and rat.
Figure 3A:
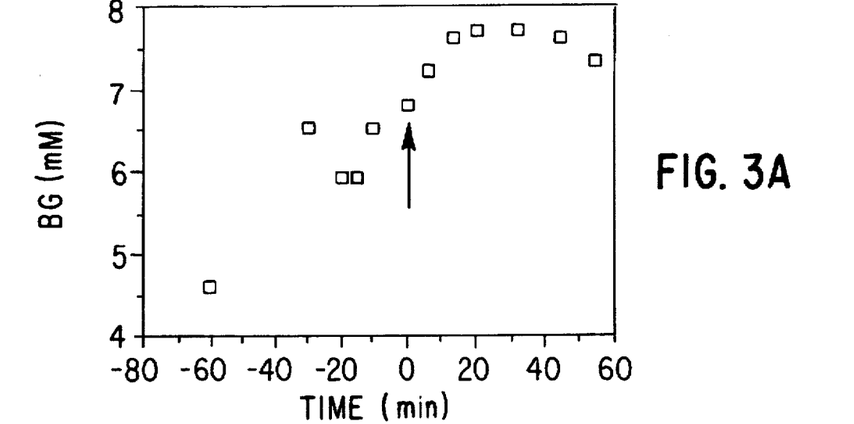
FIGS. 3A–C show the effect of administration of human galanin on levels of blood glucose (BG; (3a) 350 µg and (3b) 250 µg) and serum insulin levels (3c 250 µg) in the conscious rat. The arrow indicates the time point at which the galanin was administered.
Figure 3B:
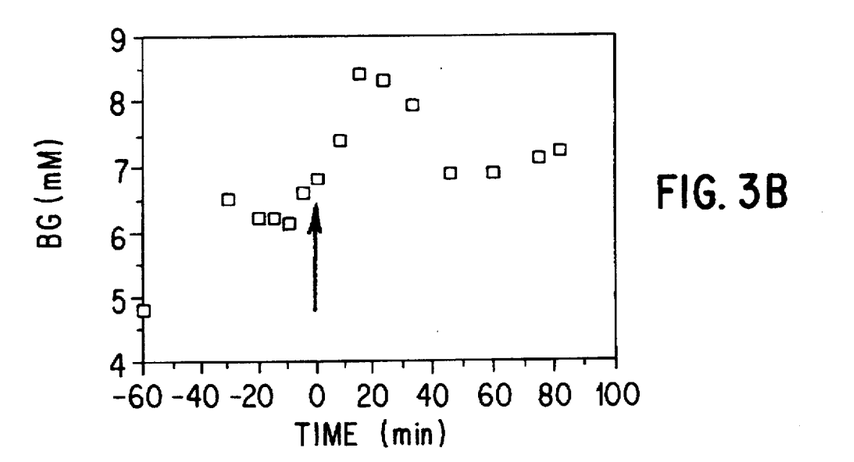
Figure 3C:
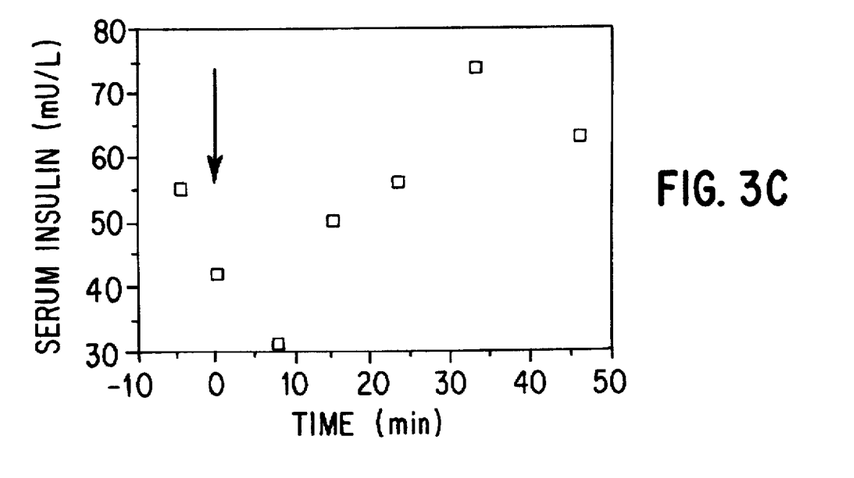

An elevation of blood glucose levels was observed in response to bolus administration of 350 μg (110 nmol; FIG. 2a) and 250 μg (80 nmol; FIG. 2b) human galanin. the elevation of blood glucose levels in response to the administration of 250 μg (80 nmol in FIG. 2c) human galanin correlates with a drop in levels of circulating insulin.

Growth Hormone Secretion

Infusion of Human Galanin into Humans

Figure 4:
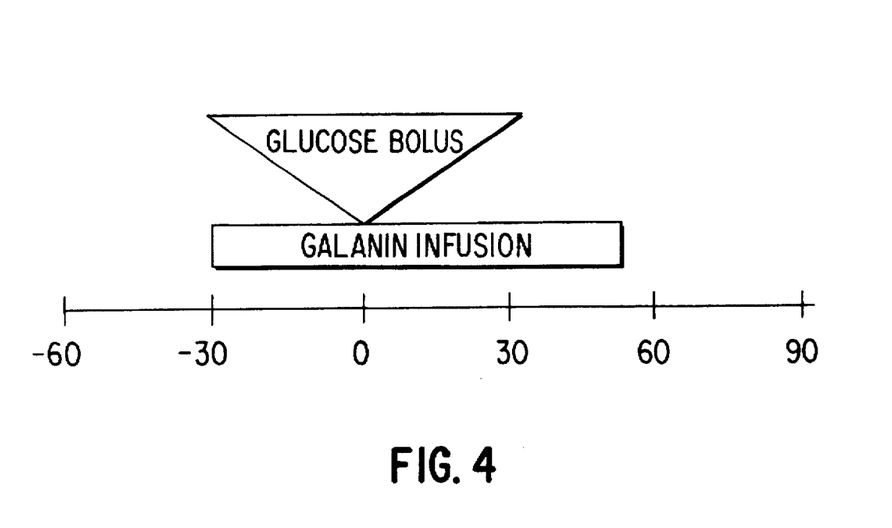
FIG. 4 shows the experimental protocol for infusion of human galanin into humans.
Figure 6:
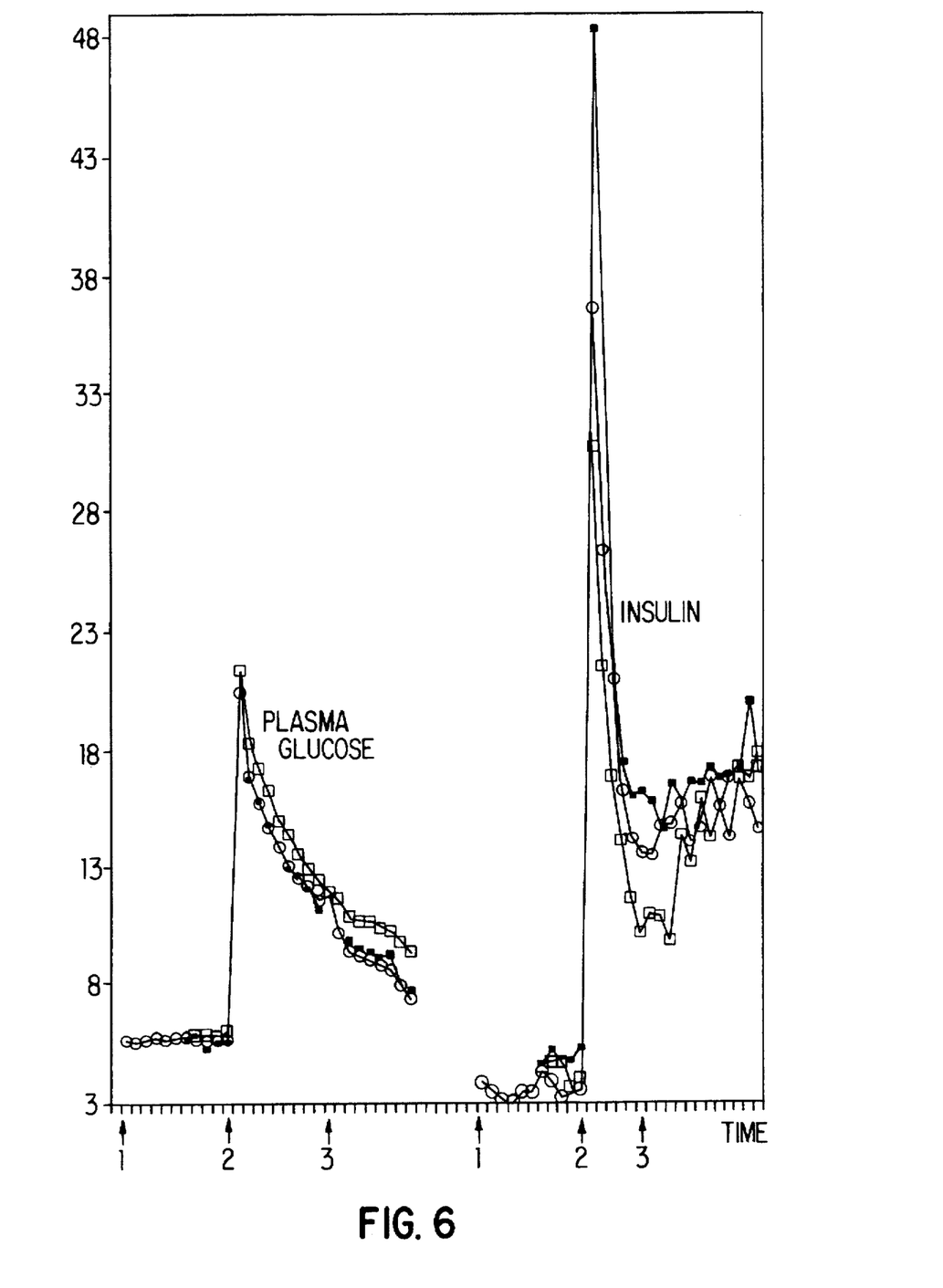
FIG. 6 shows the effect of administration of human galanin on plasma glucose and insulin levels in a human subject (–●–saline; –○–1×10⁻⁹M human galanin –□–3–4× 10⁻⁹M human galanin; Arrows 1 and 3 show commencement and stoppage of galanin infusion respectively and arrow 2 shows when glucose administered).

The experimental protocol for the infusion of human galanin into humans to achieve maximal circulating levels of galanin of approximately 3–4×10⁻⁹M is shown in FIG. 4. The effect of human galanin on blood glucose and secretion of glucoregulatory hormones in humans Preliminary data for one subject indicate that the administration of human galanin according to the protocol described in FIG. 4, to achieve maximal circulating levels of 1×10⁻⁹M and 4×10⁻⁹M human galanin, resulted in a detectable suppression of insulin secretion (FIG. 6; Y-Axis units: mIU/L). This was associated with an elevation of plasma glucose relative to the control situation (FIG. 6; Y-Axis units: mM).

The effect of human galanin on growth hormone secretion

Figure 7:
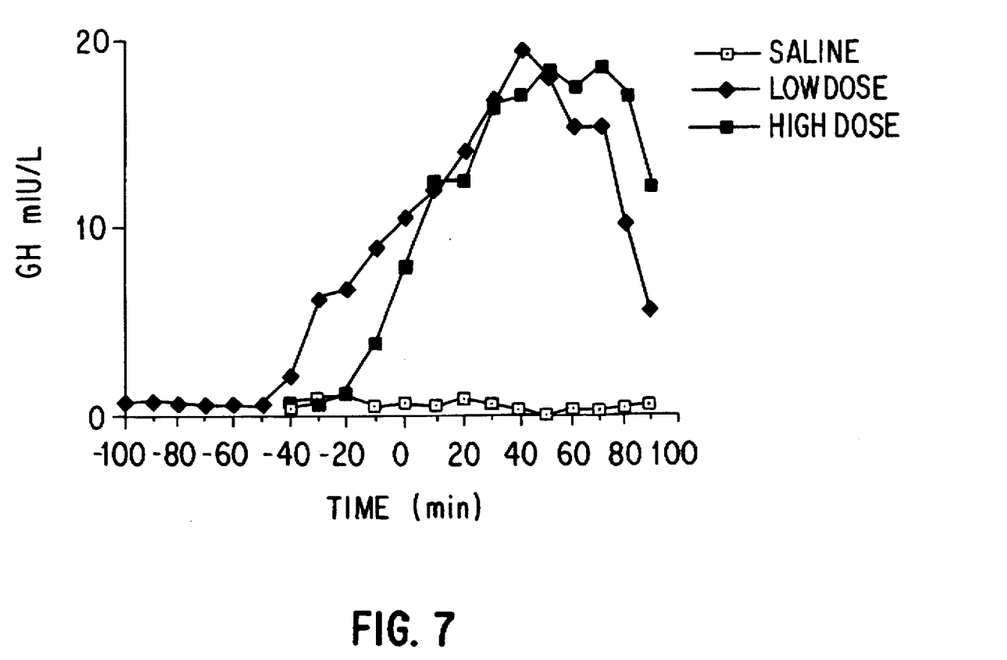
FIG. 7 shows the effect of administration of human galanin or growth hormone levels in a human subject (–□–saline; –●–1×10⁻⁹M human galanin; –■–3–4×10⁻⁹M human galanin).

The adminstration of human galanin to human volunteers according to the protocol described in FIG. 4 resulted in an elevation of growth hormone levels at circulating levels of both 1×10⁹M and 3–4×10⁻⁹M human galanin in the two subjects studied to date. The effect of human galanin in one of these two subjects at the two dosage rates employed is shown in FIG. 7.

Cardiovascular Effects

The effect of human galanin on blood pressure and vagal nerve function in the anaesthetised cat The intravenous injection of human galanin into anaesthetised cats resulted in an attenuation of cardiac vagal slowing of heart rate.

Cardiovascular effect of human aalanin in humans

Figure 5:
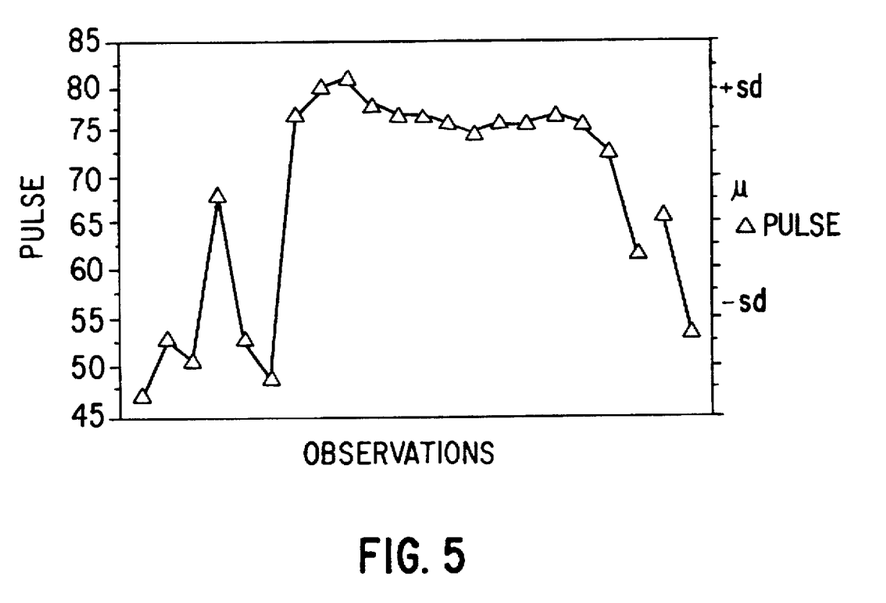
FIG. 5 shows the effect of administration of human galanin on pulse rate in a human subject.

The infusion of human galanin into humans as detailed in FIG. 4 resulted in an increase in pulse rate (see FIG. 5), consistent with an effect of human galanin on attenuation of vagal function in the human.

From studies conducted to date it is believed that human galanin will have a number of therapeutic uses including:

1. Inhibition of gastrointestinal activity, e.g. as an antidiarrhea agent.
2. Inhibition of insulin secretion e.g. modulate activity of endocrine pancreas in pancreatic disorders.
3. As a potent stimulator of growth hormone which acts independently of growth hormone releasing hormone.
4. As an attenuator of cardiac vagal function.
5. As yet not well characterised effects in the nervous system e.g. its depletion in Alzeimers disease, effects on appetite, prolactin release etc.

Experiments conducted using rat models support the first three uses, while studies in humans set out above with human galanin demonstrate the ability of human galanin to modulate insulin secretion, growth hormone secretion and cardiac vagal functions.

Prior to the present invention the possible therapeutic uses of galanin were largely restricted due to the species specific pharmacological action of galanin i.e. exogenous human galanin when administered to humans would have a different pharmacological effect than commercially available pig and rat galanin. Prior to the present invention the reasons for this species specificity was not understood. It is now believed that the species specificity is due, at least in part, to the several amino acid striking differences between human galanin and that of other species and of particular note is not extended by glycine at its C-terminal, and that in its place is a serine residue which excludes the possibility of amidation after post-translational cleavage in vivo.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. K. Tatemoto, A. Rokaeus, H. Jornvall, T. J. McDonald and V. Mutt, FEBS Lett. 164,124 (1983).
2. L. M. Kaplan, E. R. Spindel K. J. Isselbacher and W. W. Chin, Proc. Natl. Acad. Sci. U.S.A. 85, 1065 (1988).
3. A. Rokaeus and M. J. Brownstein, Proc. Natl. Acad. Sci. U.S.A., 83, 6287 (1983).
4. A. Rokaeus and M. Carlquist, FEBS Lett., 234, 400 (1988).
5. A. Rokaeus, T. Melander, T. Hokfelt, J. M. Lundberg, K. Tatemoto, M. Carlquist and V. Mutt, Neurosci. Lett, 47,161 (1984).
6. A. L. Gundlach, W. Wisden, B. J. Morris and S. P. Hunt, Neurosci. Lett., 114, 241 (1990).
7. M. F. Beal, S. M. Gabriel, K. J. Swartz, U. M. MacGarvey, Peptides, 9, 847 (1988).
8. S .M. Gabriel, L. M. Kaplan, J. B. Martin and J. I. Koenig, Peptides, 10, 369 (1989).

9. L. M. Kaplan, S. M. Gabriel, J. I. Koenig, M. E. Sunday, E. R. Spindel, B. J. Martin, W. W. Chin, Proc. Natl. Acad. Sci. U.S.A., 85, 7408 (1988).
10. T. Melander and W. A. Staines, Neurosci. Lett., 68,17 (1986); M. J. Brownstein, E. Mezey, Progress in Brain Research, Vol. 68, (EDS.T. Hokfelt, K. Fuxe and B. Pernow), 161–168, Elsevier.
11. T. Melander, W. A. Staines, T. Hokfelt, A. Rokaeus, F. Eckenstein, P. M. Salvaterra and B. H. Wainer, Brain Research, 360, 130 (1985).
12. V. Chan-Palay, J. Comp. Neurol. 243, 543 (1988); J. H. Kordower and E. J. Murfson, J. Comp. Neirol. 294,281 (1990).
13. A. Ottlecz, W. K. Sampson, S. M. McCann, Peptides, 51 (1986).
14. S. E. Kyrkoulii, B. G. Stanley and S. F. Leibowitz, Eur. J. Pharmacol. 122, 159 (1986).
15. B. E. Dunning, B. Ahren, R. C. Veith, G. Bottcher, F. Sundler, G. J. Taborsky, Am. J. Physiol. 251,14: E127 (1986)
16. A. Cheung, J. M. Polak, F. E. Bauer, A. Cadieux, N. P. Christophides, D. R. Springall, S. R. Bloom, Thorax, 40, 889 (1985).
17. F. E. Bauer, N. D. Christophides, G. W. Hacker, M. A. Blank, J. M. Polank, S. R. Bloom, Peptides, 7, 5 (1986).
18. P. Miralles, E. Piero, P. Degano, A. Ranona, J. Marco, Diabetes, 39, 996 (1990).
19. T. Messel, E. Harling, G. Bottcher, A. H. Johnsen, J. J. Holst, Regulatory Peptides, 28, 161 (1990).
20. S. G. Gilby, J. Stephenson, D. J. O'Halloran, J. M. Burrin, S. R. Bloom, Diabetes, 38, 1114 (1989).
21. M. J. Dunne, M. J. Bullet, L. Guochong, C. B. Wollheim, O. H. Petersen, EMBO, 8, 413 (1989).
22. E. Ekblad, R. Hakanson, F. Sundler, C. Wahlestedt, Br. J. Pharmacol, 86, 241 (1985); J. E. T., B. Brooks, T. J. McDonald, W. Barnett, F. Kostolanska, C. Yanaihara, A. Rokaeus, Peptides, 9, 1183 (1988).
23. B. Amiranoff, A. L. Servin, C. R. Rouyer-Fessard, A. Couvineau, K. Tatemoto and M. Luburthe, Endocrinology, 12, 284 (1987).
24. G. Skofitsch, M. Sills, D. M. Jacobowitz, Peptides, 7, 1029 (1986); T. Melander, T. Hokfelt, S. Nelsson, E. Brodin, Eur. J. Pharm., 124, 381 (1986).
25. C. Kohler, G. Hallmann, T. Melander, T. Hokfelt, E. Northeim, J. Chem. Neuro Anat. 2, 269 (1989).
26. B. Gallwitz, W. E. Shimdt, R. Schwarzhoff, W. Creutzfeldt, Biochem. and Biophys. Res. Communications, 172, 268 (1990); B. Amiranoff, A. M. Lorinet, N. Yanaihara, M. Laburthe, Eur. J. Pharm., 163, 205 (1989).
27. W. J. Rossowski, T. M. Rossowski, S. Zacharia, A. Ertan and D. H. Coy, Peptides, 11, 333, (1990).

---

We claim:

1. A method of modulating insulin secretion in a human subject comprising administering to the subject a therapeutically effective amount of the peptide as shown in SEQ ID NO:1.

2. A cDNA molecule encoding a peptide having a sequence as shown in SEQ ID NO: SEQ ID NO:1, wherein the cDNA molecule has a sequence as shown in SEQ ID NO:8 from nucleotide 110 to 199 or from nucleotide 110 to 158.

3. A DNA molecule encoding human preprogalanin and galanin mRNA associate peptide, the DNA molecule having a sequence as shown in SEQ ID NO. 8.

4. A method of producing human galanin comprising transforming a cell with the DNA molecule of claim 2 such that the DNA is operatively linked to a promoter and culturing the transformed cell under conditions which allow the expression of the DNA sequence and recovering the human galanin produced.

5. A method as claimed in claim 4 in which the cell is a bacterial cell.

* * * * *

UNITED STATES PATENT AND TRADEMARK OFFICE
CERTIFICATE OF CORRECTION

PATENT NO. : 5,756,460
DATED : May 26, 1998
INVENTOR(S) : Helen Frances Evans et al.

It is certified that error appears in the above-indentified patent and that said Letters Patent is hereby corrected as shown below:

<u>In the Figures:</u> Col. 5, line 50, "porcine, (SEQ ID NO:4) and rat;" should be -- porcine (SEQ ID NO:3), and rat (SEQ ID NO:4); --;

<u>In the Claims:</u> Col. 15, line 61, delete "SEQ ID NO:" (first occurrence).

Signed and Sealed this

Fourth Day of May, 1999

Attest:

Q. TODD DICKINSON

*Attesting Officer*    *Acting Commissioner of Patents and Trademarks*